United States Patent [19]
Kao et al.

[11] Patent Number: 5,530,007
[45] Date of Patent: Jun. 25, 1996

[54] CARBAMATES OF RAPAMYCIN

[75] Inventors: Wenling Kao, Paoli; Magid A. Abou-Gharbia, Glen Mills, both of Pa.; Robert L. Vogel, Stratford, N.J.

[73] Assignee: American Home Products Corporation, Madison, N.J.

[21] Appl. No.: 402,590

[22] Filed: Mar. 13, 1995

Related U.S. Application Data

[60] Division of Ser. No. 297,663, Sep. 1, 1994, Pat. No. 5,480,989, which is a continuation-in-part of Ser. No. 160,984, Dec. 1, 1993, abandoned, which is a division of Ser. No. 54,655, Apr. 23, 1993, Pat. No. 5,302,584, which is a continuation-in-part of Ser. No. 960,597, Oct. 13, 1992, abandoned.

[51] Int. Cl.⁶ ........................ A61K 31/395; C07D 498/16
[52] U.S. Cl. ........................................ 514/291; 540/456
[58] Field of Search ............................. 514/291; 540/546

[56] References Cited

U.S. PATENT DOCUMENTS

| | | | |
|---|---|---|---|
| 3,929,992 | 12/1975 | Sehgal et al. | 514/291 |
| 3,993,749 | 11/1976 | Sehgal et al. | |
| 4,316,885 | 2/1982 | Rakhit | |
| 4,375,464 | 3/1983 | Sehgal et al. | |
| 4,401,653 | 8/1983 | Eng | |
| 4,650,803 | 3/1987 | Stella et al. | |
| 4,885,171 | 12/1989 | Surendra et al. | |
| 5,023,262 | 6/1991 | Caufield et al. | |
| 5,023,263 | 6/1991 | Von Burg | |
| 5,023,264 | 6/1991 | Caufield et al. | |
| 5,078,999 | 1/1992 | Warner et al. | |
| 5,080,899 | 1/1992 | Sturm et al. | 514/291 |
| 5,091,389 | 2/1992 | Ondeyka et al. | 514/291 |
| 5,100,883 | 3/1992 | Schiehser | 514/291 |
| 5,100,899 | 3/1992 | Calne | 514/291 |
| 5,102,876 | 4/1992 | Caufield | 514/291 |
| 5,118,677 | 6/1992 | Caufield | 514/291 |
| 5,118,678 | 6/1992 | Kao et al. | 514/291 |
| 5,120,842 | 6/1992 | Failli et al. | 514/291 |
| 5,130,307 | 7/1992 | Failli et al. | 514/291 |
| 5,138,051 | 8/1992 | Hughes et al. | 514/291 |
| 5,151,413 | 9/1992 | Caufield et al. | 514/291 |
| 5,169,851 | 12/1992 | Hughes et al. | 514/291 |
| 5,177,203 | 1/1993 | Failli et al. | 514/291 |
| 5,194,447 | 3/1993 | Kao | 514/291 |
| 5,221,670 | 6/1993 | Caufield | 514/291 |
| 5,233,036 | 8/1993 | Hughes | 514/291 |
| 5,260,300 | 11/1993 | Hu | 514/291 |
| 5,262,423 | 11/1993 | Kao | 514/291 |
| 5,286,730 | 2/1994 | Caufield et al. | 514/291 |
| 5,286,731 | 2/1994 | Caufield et al. | |
| 5,302,584 | 4/1994 | Kao et al. | 514/291 |

FOREIGN PATENT DOCUMENTS

507555A1 7/1992 European Pat. Off. .
WO9113899 9/1991 WIPO ................................. 514/291

OTHER PUBLICATIONS

Venzina, C., J. Antibiot. 28:721 (1975).
Sehgal, S. N., J. Antibiot. 28:727 (1975).
Baker, H. J., Antibiot. 31:539 (1978).
Martel, R. R., Can. J. Physiol. Pharmacol. 55:48 (1977).
Staruch, M. J., FASEB 3:3411 (1989).
Dumont, F. J., FASEB 3:5256 (1989).
Calne, R. Y., Lancet 1183 (1978).
Morris, R. E., Med. Sci. Res. 17:877 (1989).
Baeder, W. L., Fifth Int. Conf. Inflamm. Res. Assoc. 121 (Abstract) (1990).
Meiser, B. M., J. Heart Lung Transplant. 11 (pt. 2):197 (1992).
Stepkowski, S. M., Transplantation Proc. 23:507 (1991).

Primary Examiner—Robert T. Bond
Attorney, Agent, or Firm—Arnold S. Milowsky

[57] ABSTRACT

A compound of the structure

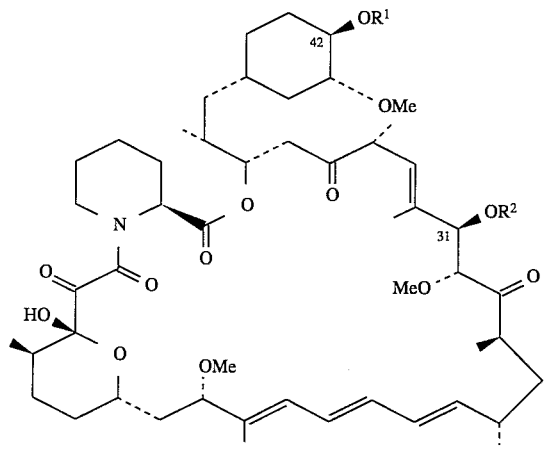

wherein $R^1$ and $R^2$ are each, independently, hydrogen, —CONH—$[(CR^3R^4)_m(-A-(CR^5R^6)_n)_p]_q$—B;

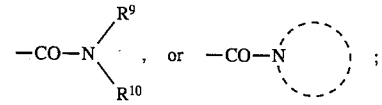

The remaining terms are defined in the specification. The compounds are useful as antitumor, antiinflammatory, antifungal, antiproliferative and immunosuppressive agents.

1 Claim, No Drawings

CARBAMATES OF RAPAMYCIN

This is a division of application Ser. No. 08/297,663 filed Sep. 1, 1994, now U.S. Pat. No. 5,480,989, which is a continuation-in-part of Ser. No. 08/160,984, filed Dec. 1, 1993, which is a divisional of Ser. No. 08/054,655, filed Apr. 23, 1993, (now U.S. Pat. No. 5,302,584), which is a continuation-in-part of Ser. No. 07/960,597, filed Oct. 13, 1992, abandoned.

BACKGROUND OF THE INVENTION

This invention relates to carbamates of rapamycin and a method for using them for inducing immunosuppression, and in the treatment of transplantation rejection, host vs. graft disease, autoimmune diseases, diseases of inflammation, solid tumors, fungal infections, and hyperproliferative vascular disorders.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31,539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); R. Y. Calne et al., Lancet 1183 (1978); and U.S. Pat. No. 5,100,899].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990)], and smooth muscle cell proliferation and intimal thickening following vascular injury [Morris, R. J. Heart Lung Transplant 11 (pt. 2): 197 (1992)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42- positions. U.S. Pat. No. 5,118,678 discloses carbamates of rapamycin that are useful as immunosuppressive, anti-inflammatory, antifungal, and antitumor agents.

DESCRIPTION OF THE INVENTION

This invention provides derivatives of rapamycin which are useful as immunosuppressive, antiinflammatory, antifungal, antiproliferative, and antitumor agents having the structure

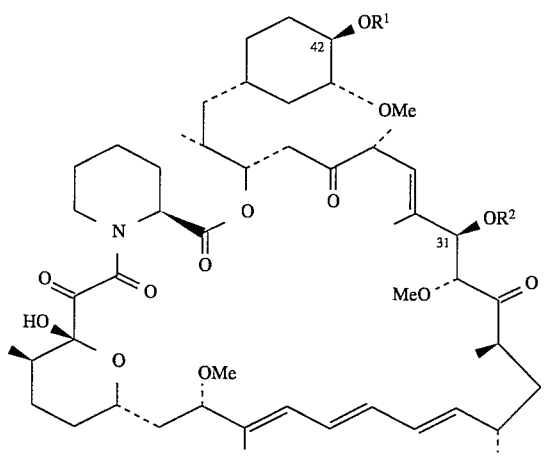

wherein $R^1$ and $R^2$ are each, independently, hydrogen, $-CONH-[(CR^3R^4)_m(-A-(CR^5R^6)_n)_p]_q-B$;

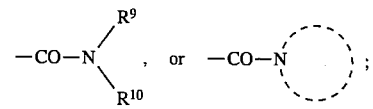

$R^3$, $R^4$, $R^5$, $R^6$, and B are each, independently, hydrogen, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, arylalkyl of 7–10 carbon atoms, cycloalkyl of 3–8 carbon atoms, $-OR^7$, $-SR^7$, halogen, $-CN$, $-NO_2$, $-CF_3$, $-COR^7$, $-CO_2R^7$, $-CONHR^7$, $-SO_2R^7$, $-OSO_3R^7$, $-NR^7R^8$, $-NHCOR^7$, $-NHSO_2R^7$, or Ar;

$R^7$ and $R^8$ are each, independently, hydrogen, alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, cycloalkyl of 3–8 carbon atoms, or Ar;

$R^9$ and $R^{10}$ are each, independently, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, arylalkyl of 7–10 carbon atoms, cycloalkyl of 3–8 carbon atoms, $-CF_3$, $-COR^7$, $-CO_2R^7$, $-CONHR^7$, $-SO_2R^7$, or Ar;

A is $-CH_2-$, $-NR^7-$, $-O-$, $-S-$, $-SO-$, $-SO_2-$, $-PR^7-$, $-CO-$, $-NHCO-$, $-NHSO-$, or $-P(O)(R^7)-$;

Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, indolyl, thiazolyl, isoxazolyl, pyrimidinyl, pyrazinyl, imidazolyl, benzopyranyl, benz[b] thiophenolyl, benzimidazolyl, benzthiazolyl, benzodioxolyl, piperidinyl, morpholinyl, piperazinyl, tetrahydrofuranyl, or pyrrolidinyl; wherein the Ar group may be optionally mono-, di-, or tri-substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, —PO$_3$H, and —CO$_2$H;

is a nitrogen containing heterocycle that may be saturated, unsaturated, or partially unsaturated, and may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO$_3$H, —PO$_3$H, and —CO$_2$H; with the proviso that $R^1$ and $R^2$ are not both hydrogen; m=0–6; n=0–6; p=0–1; q=0–1; or a pharmaceutically acceptable salt thereof.

The pharmaceutically acceptable salts are those derived from such inorganic cations such as sodium, potassium, and the like; organic bases such as: mono-, di-, and trialkyl amines of 1–6 carbon atoms, per alkyl group and mono-, di-, and trihydroxyalkyl amines of 1–6 carbon atoms per alkyl group, and the like; and organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

It is preferred that the aryl portion of the arylalkyl substituent is a phenyl, piperazinyl, piperidinyl, or pyridyl group that is optionally mono-, di-, or tri-substituted with a group selected from alkyl of 1–6 carbon atoms, arylalkyl of 7–10 carbon atoms, alkoxy of 1–6 carbon atoms, cyano, halo, nitro, carbalkoxy of 2–7 carbon atoms, trifluoromethyl, amino, dialkylamino of 1–6 carbon atoms per alkyl group, alkylthio of 1–6 carbon atoms, —SO$_3$H, —PO$_3$H, and —CO$_2$H.

It is preferred that

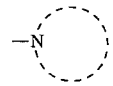

is a pyridyl, pyrazinyl, piperidinyl, morpholinyl, piperazinyl, pyrrolidinyl, thiazolyl, pyrimidinyl, isoxazolyl, pyrrolidinyl, or imidazolyl group that may be optionally substituted as described above.

Preferred members include those compounds in which $R^2$ is hydrogen; those in which p=0 and B is Ar; those in which p=0, B is Ar, and $R^2$ is hydrogen; those in which p=0, B is Ar, $R^2$ is hydrogen, and Ar is pyridyl, furyl, piperazinyl, piperazinyl, morpholinyl, and piperidinyl; those in which m=0–3 and p=0; those in which m=2, n=0, p=1, q=1 and A is —O— or NR$^7$;

those in which $R^1$ is

and $R^2$ is hydrogen; and those in which $R^1$ is

, $R^2$ is hydrogen, and

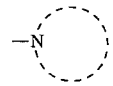

is an optionally substituted morpholinyl or piperazinyl group.

Of these compounds, preferred members also include those having the structure

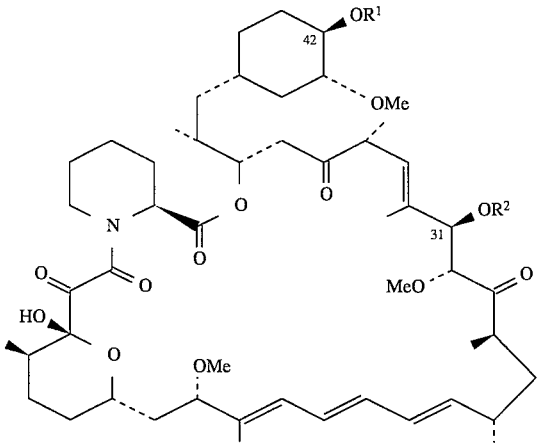

wherein $R^1$ and $R^2$ are each, independently, hydrogen, or —CONH—[(CR$^3$R$^4$)$_m$(—A—(CR$^5$R$^6$)$_n$)$_p$]$_q$—B;

$R^3$, $R^4$, $R^5$, $R^6$, and B are each, independently, hydrogen, alkyl of 1–6 carbon atoms, arylalkyl of 7–10 carbon atoms, cycloalkyl of 3–8 carbon atoms, —OR$^7$, —SR$^7$, halogen, —CN, —NO$_2$, —CF$_3$, —COR$_7$, —CONH$_2$, —SO$_2$R$_7$, —OSO$_3$R$^7$, —NR$^7$R$^8$, —NHCOR$^7$, —NHSO$_2$R$^8$, or Ar;

A is —CH$_2$—, —NR$^7$—, —O—, —S—, —SO$_2$—, —PR$^7$—, or —P(O)(R$^7$)—;

$R^7$ and $R^8$ are each, independently, hydrogen, alkyl of 1–6 carbon atoms, arylalkyl of 7–10 carbon atoms, or Ar;

Ar is phenyl, naphthyl, pyridyl, quinolyl, isoquinolyl, quinoxalyl, thienyl, thionaphthyl, furyl, benzofuryl, benzodioxyl, benzoxazolyl, benzoisoxazolyl, or benzodioxolyl; wherein the Ar group may be optionally mono-, di-, or tri-substituted with a group selected from alkyl of 1–6 carbon atoms, arylalkyl of 7–10 carbon atoms, alkoxy of 1–6 carbon atoms, cyano, halo, nitro, carbalkoxy of 2–7 carbon atoms, trifluoromethyl, amino, dialkylamino of 1–6 carbon atoms per alkyl group, alkylthio of 1–6 carbon atoms, —SO$_3$H, —PO$_3$H, and —CO$_2$H;

with the proviso that $R^1$ and $R^2$ are not both hydrogen; m=0–6;

n=0–6;
p=0–1;
q=0–1;
or a pharmaceutically acceptable salt thereof.

The compounds of this invention carbamylated at the 42-position or at both the 31- and 42-positions can be prepared by converting the 42- and/or 31-alcohols of rapamycin to a carbonate followed by reaction with an appropriately substituted amine to provide the desired carbamate. This scheme is illustrated below for the preparation of the compound of Example 3.

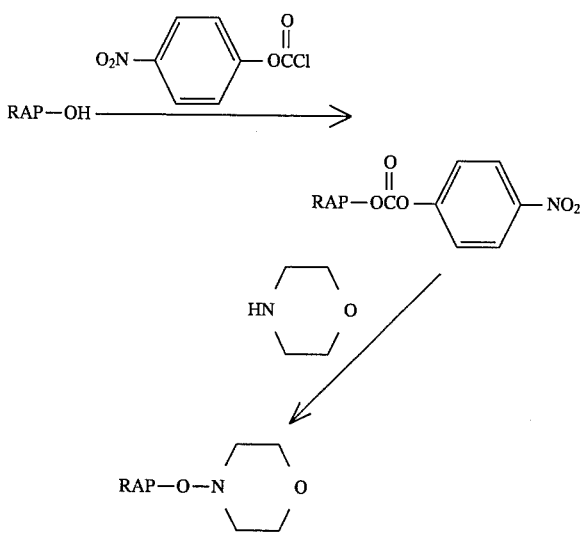

Alternatively the compounds of this invention carbamylated at the 42-position or at both the 31- and 42-positions can be prepared by reacting rapamycin with an appropriately substituted isocyanate under neutral conditions or in the presence of a base, such as pyridine. Preparation of carbamates of rapamycin using this method was disclosed in U.S. Pat. No. 5,118,678, which is hereby incorporated by reference.

The 31-carbamylated compounds of this invention can be prepared by protecting the 42-alcohol of rapamycin with a protecting group, such as with a tert-butyl dimethytsilyl group, followed by carbamylation of the 31-position by the procedures described above. Removal of the protecting group provides the 31-carbamylated compounds. In the case of the tert-butyl dimethylsilyl protecting group, deprotection can be accomplished under mildly acidic conditions.

Having the 31-position carbamylated and the 42-position deprotected, the 42-position can be carbamylated using a different amine (via the carbonate) or isocyanate than was reacted with the 31-alcohol, to give compounds having different carbamates at the 31- and 42- positions. Alternatively, the 42-carbamylated compounds, prepared as described above, can be reacted with a different amine (via the carbonate) or isocyanate to provide compounds having different carbamates at the 31- and 42-positions.

The amines and isocyanates used to prepare the compounds of the invention are commercially available or can be prepared by methods that are disclosed in the literature.

This invention also covers analogous carbamates of other rapamycins such as, but not limited to, 29-demethoxyrapamycin, [U.S. Pat. No. 4,375,464, 32-demethoxyrapamycin under C.A. nomenclature]; rapamycin derivatives in which the double bonds in the 1-, 3-, and/or 5-positions have been reduced [U.S. Pat. No. 5,023,262]; 42-oxorapamycin [U.S. Pat. No. 5,023,262]; 29-desmethylrapamycin [U.S. Pat. No. 5,093,339, 32-desmethylrapamycin under C.A. nomenclature]; 7,29-bisdesmethylrapamycin [U.S. Pat. No. 5,093,338, 7,32-desmethylrapamycin under C.A. nomenclature]; and 15-hydroxyo and 15,27-bishydroxy- rapamycin [U.S. Pat. No. 5,102,876]. The disclosures in the above cited U.S. Patents are hereby incorporated by reference.

Immunosuppressive activity for representative compounds of this invention was evaluated in an in vitro standard pharmacological test procedure to measure lymphocyte proliferation (LAF) and in an in vivo standard pharmacological test procedure which evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. For each compound evaluated, rapamycin was also evaluated for the purpose of comparison. An $IC_{50}$ was obtained for each test compound as well as for rapamycin. When evaluated as a comparator for the representative compounds of this invention, rapamycin had an $IC_{50}$ ranging from 0.3–4.6 nM. The results obtained for the representative compounds of this invention were also expressed as a ratio compared with rapamycin. A positive ratio indicates immunosuppressive activity. A ratio of greater than 1 indicates that the test compound inhibited thymocyte proliferation to a greater extent than rapamycin. Calculation of the ratio is shown below.

$$\frac{IC_{50} \text{ of Rapamycin}}{IC_{50} \text{ of Test Compound}}$$

Representative compounds of this invention were also evaluated in an in vivo test procedure designed to determine the survival time of pinch skin graft from male BALB/c donors transplanted to male C₃H(H—2K) recipients. The method is adapted from Billingham R. E. and Medawar P. B., J. Exp. Biol. 28:385–402, (1951). Briefly, a pinch skin graft from the donor was grafted on the dorsum of the recipient as an allograft, and an isograft was used as control in the same region. The recipients were treated with varying concentrations of either test compounds intraperitoneally or orally. Rapamycin was used as a test control. Untreated recipients served as rejection control. The graft was monitored daily and observations were recorded until the graft became dry and formed a blackened scab. This was considered as the rejection day. The mean graft survival time (number of days±S.D.) of the drug treatment group was compared with the control group. The following table shows the results that were obtained. Results are expressed as the mean survival time in days. Untreated (control) pinch skin grafts are usually rejected within 6–7 days. The results shown in Table 1 are based on a dose of 4 mg/kg of test compound. A survival time of 12.0±1.7 days was obtained for rapamycin at 4 mg/kg.

The following table summarizes the results of representative compounds of this invention in these two standard test procedures.

TABLE 1

EVALUATION OF IMMUNOSUPPRESSIVE ACTIVITY*

| Compound | LAF $IC_{50}$ (nM) | LAF (ratio) | Skin Graft (days ± SD) |
|---|---|---|---|
| Example 2 | 3.4 | 1.4 | 11.2 ± 1.0 |
|  | 0.4 | 1.1 | 10.0 ± 0.9 |
| Example 3 | 0.2 | 6.2 | 9.7 ± 0.8 |
| Example 4 | 1.2 | 1.2 | 10.0 ± 0.0 |
|  | 0.6 | 1.0 |  |
|  | 1.2 | 0.5 |  |
| Example 5 | 1.5 | 0.6 | 11.2 ± 1.2 |
| Example 6 | 4.1 | 1.1 | 12.0 ± 1.0 |
| Example 7 | 1.1 | 1.5 | 9.3 ± 0.8 |
|  | 0.9 | 1.0 |  |
| Example 8 | 6.5 | 0.3 |  |
| Example 9 | 0.2 | 1.1 | 8.7 ± 0.5 |
| Example 11 | 1.9 | 0.26 | 12.6 ± 1.5 |
|  | 2.2 | 0.4 | 12.0 ± 0.6 |
|  | 1.9 | 0.5 |  |
| Example 12 | 2.8 | 0.4 | 12.4 ± 0.9 |
|  | 3.0 | 0.9 | 11.0 ± 1.7 |
| Example 13 | 1.0 | 0.5 | 11.2 ± 0.7 |
|  | 1.9 | 0.4 | 11.7 ± 1.6 |
| Example 14 | 1.2 | 0.6 | 13.6 ± 0.6 |
|  | 2.2 | 0.4 |  |
|  | 3.0 | 0.8 |  |
|  | 1.4 | 0.5 |  |
| Example 15 | 3.5 | 0.7 |  |
| Example 16 | 4.0 | 0.6 |  |
| Example 17 | 0.8 | 0.9 | 11.8 ± 1.5 |
| Example 18 | 1.6 | 0.4 | 13.0 ± 0.7 |
|  | 1.0 | 0.7 |  |
| Example 21 | 0.9 | 0.6 | 11.0 ± 1.1 |
|  | 1.4 | 0.8 |  |
|  | 1.6 | 0.6 |  |
| Example 22 | 0.5 | 0.9 | 10.8 ± 1.2 |
|  | 1.9 | 0.3 |  |
| Example 23 | 0.9 | 0.4 | 9.2 ± 1.5 |
| Example 24 | 1.8 | 0.5 | 8.7 ± 1.0 |
| Example 25 | 0.5 | 1.8 | 11.7 ± 0.8 |
|  | 2.6 | 0.9 |  |
|  | 1.9 | 0.8 |  |
| Example 26 | 0.9 | 1.1 | 12.5 ± 0.6 |
|  | 0.7 | 0.9 |  |
| Example 27 | 1.9 | 1.3 |  |
| Example 28 | 2.3 | 1.0 |  |
| Example 29 | 1.6 | 0.9 |  |
| Example 30 | 1.7 | 0.9 |  |
| Example 32 | 2.6 | 0.6 |  |
| Example 33 | 1.6 | 0.9 |  |
| Example 36 | 0.7 | 1.3 | 11.3 ± 0.8 |
| Example 37 | 5.1 | 0.6 | 13.0 ± 0.6 |
|  |  |  | 10.2 ± 1.2 |
| Example 38 | 2.4 | 0.5 | 11.3 ± 1.0 |
| Example 39 | 2.6 | 0.4 | 10.8 ± 1.2 |
| Example 40 | 4.8 | 0.2 | 11.2 ± 1.3 |
| Example 41 | 18.0 | 0.1 | 11.3 ± 1.6 |
| Example 42 | 0.5 | 1.6 |  |
|  | 2.2 | 1.1 |  |
| Example 43 | 0.3 | 1.7 | 9.0 ± 0.0 |
| Example 44 | 0.7 | 0.7 |  |
| Example 45 | 0.5 | 0.8 | 8.3 ± 0.5 |
| Example 46 | 2.0 | 0.4 | 7.5 ± 0.5 |
| Example 47 | 12.0 | 0.1 | 7.5 ± 0.8 |

*Calculation of the ratio was described supra.

The results of these standard pharmacological test procedures demonstrate immunosuppressive activity both in vitro and in vivo for the compounds of this invention. Positive ratios in the LAF test procedures indicates suppression of T-cell proliferation, thereby demonstrating the immunosuppressive activity of the compounds of this invention. As transplanted pinch skin grafts are typically rejected within 6–7 days without the use of an immunosuppressive agent, the increased survival time of the skin graft when treated with the compounds of this invention further demonstrates their utility as immunosuppressive agents and as agents useful in the treatment or prevention of transplantation rejection.

Representative compounds of this invention were also evaluated in the adjuvant arthritis standard pharmacological test procedure, which measures the ability of the compound tested to inhibit immune mediated inflammation. The adjuvant arthritis test procedure is a standard pharmacological test procedure for rheumatoid arthritis. The procedure used and results obtained are described below The adjuvant arthritis standard pharmacological test procedure measures the ability of test compounds to prevent immune mediated inflammation and inhibit or treat rheumatoid arthritis. The following briefly describes the test procedure used. A group of rats (male inbread Wistar Lewis rats) are pre-treated with the compound to be tested (1 h prior to antigen) and then injected with Freud's Complete Adjuvant (FCA) in the right hind paw to induce arthritis. The rats are then orally dosed on a Monday, Wednesday, Friday schedule from day 0–14 for a total of 7 doses. Both hind paws are measured on days 16, 23, and 30. The difference in paw volume (mL) from day 16 to day 0 is determined and a percent change from control is obtained. The left hind paw (uninjected paw) inflammation is caused by T-cell mediated inflammation and is recorded in the above table (% change from control). The right hind paw inflammation, on the other hand, is caused by nonspecific inflammation. Compounds were tested at a dose of 2 mg/kg. The results are expressed as the percent change in the uninjected paw at day 16 versus control; the more negative the percent change, the more potent the compound. Rapamycin provided −70–87% change versus control, indicating that rapamycin treated rats had 70 to 87% less immune induced inflammation than control rats. The following results were obtained: Example 6, −38% change versus control; Example 14, −38 and −21% change versus control; Example 17, −30% change versus control; Example 18, −14% versus control; Example 26, −70% change versus control; and Example 13 showed no reduced inflammation at 2 mg/kg.

Based on the results of these standard pharmacological test procedures, the compounds are useful in the treatment or prevention of transplantation rejection such as kidney, heart, liver, lung, bone marrow, pancreas (islet cells), cornea, small bowel, and skin allografts, and heart valve xenografts; in the treatment of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, pulmonary inflammation, asthma, and eye uveitis.

Because of the activity profile obtained, the compounds of this invention also are considered to have antitumor, antifungal activities, and antiproliferative activities. The compounds of this invention therefore are also useful in treating solid tumors, fungal infections, and hyperproliferative vascular diseases such as restenosis and atherosclerosis.

It is contemplated that when the compounds of this invention are used as an immunosuppressive or antiinflammatory agent, they can be administered in conjunction with one or more other immunoregulatory agents. Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the compounds of this invention with such other drugs or agents for inducing immunosuppression or treating inflammatory conditions, lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23:507 (1991)].

The compounds of this invention can be formulated neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1–5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 µg/kg - 100 mg/kg, preferably between 0.001–25 mg/kg, and more preferably between 0.01–5 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is subdivided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the preparation of representative compounds of this invention.

Example 1

Rapamycin 42-nitrophenyl carbonate

A solution of 2.0 g of rapamycin in 10 ml of dichloromethane and 2 mL of dry pyridine was cooled to −78° C. under a nitrogen atmosphere. To this solution, 662 mg 4-nitrophenyl chloroformate was added; the resulting solution was stirred at room temperature under nitrogen for 20 hours. The mixture was diluted with water and extracted with dichloromethane. The dichloromethane extract was washed with water, dried over $MgSO_4$ and evaporated. The residue was chromatographed on silica gel. Elution with 33% ethyl acetate in n-hexane gave 2.07 g of rapamycin 42-p-nitrophenyl carbonate as a white foam.

Example 2

Rapamycin 42-ester with 4-(3-hydroxypropyl)piperazine-1-carboxylic acid

A solution of 130 mg (0.90 mmole) of 1-(3-hydroxypropyl)piperazine in 2 mL dichloromethane was added to a solution of 320 mg (0.30 mmole) rapamycin-42-(4-nitrophenyl)carbonate in 6 mL dichloromethane under nitrogen at −5° C. and allowed to warm to 20° with stirring. After 4 hours, the reaction mixture was partitioned between dichloromethane and water/brine. The organic portion was washed with brine and flash chromatographed through silica gel using methanol (2.0 to 3.0%) in dichloromethane, yielding 115 mg product as a white solid, mp 104°–113° C.

IR (KBr): 3430, 2930, 1715, 1640, 1450, 1240, and 985 cm$^{-1}$.
NMR (CDC13, 400 MHz): δ3.81(t (J=5.2Hz), 2H, Hd); 3.49 (broad, 4H, Ha); 3.38 (s, 3H, OMe); 3.33 (s, 3H, OMe); 3.13 (s, 3H, OMe); 2.62 (t(J=5.4 Hz), 2H, Hc); 2.48 (broad, 4H, Hb) ppm.
MS (neg ion FAB): 1083 (M—), 590.

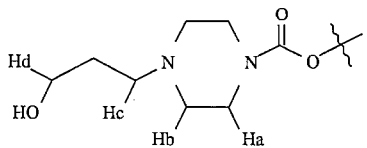

Example 3

Rapamycin 42-ester with morpholine-4-carboxylic acid

A solution of 95 mg (1.1 mmole) morpholine in 1 mL dry dichloromethane was added to a stirred solution of 330 mg (0.31 mmole) rapamycin-42-(4-nitrophenyl)carbonate in 6 mL dichloromethane at −5° C. under nitrogen; stirring was continued 4.5 hours at −5° and 2 hours at 20°. The reaction mixture was partitioned between dichloromethane and water/brine; the organic portion was washed with brine and flash chromatographed through silica gel using methanol (1.0 to 1.6%) in dichloromethane, yielding 70 mg product as a white solid, mp 105°–115° C.
IR (KBr): 3450, 2950, 1710, 1650, 1250, and 993 cm$^{-1}$.
NMR (CDC13, 400 MHz): δ3.64 (4H, 3-morpholine); 3.46 (t (J=4.9 Hz), 4H, 2-morpholine); 3.37 (s, 3H, OMe); 3.32 (s, 3H, OMe); 3.12 (s, 3H, OMe) ppm.
MS (neg ion FAB): 1026 (M—), 590.

Example 4

Rapamycin 4.2-ester with 4-methylpiperazine-1-carboxylic acid

A solution of 95 mg (0.95 mmole) 1-methylpiperazine in 2 mL dichloromethane was added to a solution of 310 mg (0.29 mmole) rapamycin-42-(4-nitrophenyl)carbonate in 6 mL dichloromethane at 0° C. under nitrogen and stirred at 0° for 2 hours and at 20° for 2 hours. The reaction mixture was partitioned between dichloromethane and water/brine. The organic portion was washed with brine and flash chromatographed through silica gel using methanol (2.0 to 3.0%) in dichloromethane, yielding 120 mg product as a white solid, mp 108°–116° C.
IR (KBr): 3450, 2945, 1710, 1650, 1460, 1240, 1110, and 990 cm$^{-1}$.
NMR (CDC13, 400 MHz): δ3.50 (broad, 4H, 2-piperazine); 3.39 (s, 3H, OMe); 3.33 (s, 3H, OMe); 3.14 (s, 3H, OMe); 2.36 (broad, 4H, 3-piperazine); 2.30 (s, 3H, NMe) ppm.
MS (neg ion FAB): 1039 (M—), 590.

Example 5

Rapamycin 42-ester with 4-methyl-piperazine-1-carboxylic acid salt with hydrochloric acid.

A solution of 720 mg rapamycin 42-ester with 4-methylpiperazine-1-carboxylic acid in a mixture of 5 ml ethyl acetate and 10 ml ether was treated at 0° under nitrogen with 0.7 ml 1M HCl (gas) in ether. The hydrochloride salt formed instantly. Stirring was continued at 0° under nitrogen for ¼ hour. The solid product was collected by filtration, washed with ether, and dried in vacuum at 55° to afford 510 mg of the title product as a white solid, mp 128°–134°.

IR (KBr): 3400 (OH, NH), 1715 (lactone and ketone C=O). 1640 (amide C=O), 450, 1260, 1100, and 980 cm$^{-1}$. $^1$HNMR (DMSO-D$_6$, 400 MHz δ4.39 (m, 1 H, C$_{42}$—H), 3.29, 3.14, 3.04 (each s, 3H, OCH$_3$), 2.74 (s, 3H, CH$_3$—N—) ppm.
MS (neg. ion FAB): 1039.6(M$^-$), 590.4, 447.4. C/H/N analysis for C$_{57}$H$_{89}$N$_3$O14·HCl·H$_2$O; Calc. 62.53/8.28/3.83; Found 62.42/8.48/3.77.

Example 6

Rapamycin 42-ester with piperazine-1-carboxylic acid

A solution of 190 mg (2.2 mmole) piperazine in 4 mL dichloromethane was added to a solution of 550 mg (0.51 mmole) rapamycin-42-(4-nitrophenyl)carbonate in 12 mL dichloromethane at 0° C. under nitrogen and stirred 45 minutes. Partitioning between dichloromethane and water/brine, washing with brine and flash chromatography through silica gel using 5% methanol in dichloromethane yielded 350 mg product as a pale yellow solid, mp 120°–131° C.
IR (KBr): 3460, 2950, 1705, 1650, 1460, 1245, and 990 cm$^{-1}$.
NMR (CDC13, 400 MHz): δ4.8 (broad, 1 H, NH); 3.46 (broad, 4H, 2piperazine); 3.39 (s, 3 H, OMe); 3.33 (s, 3 H, OMe); 3.14 (s, 3 H, OMe); 2.83 (broad, 4 H, 3-piperazine) ppm.
MS (neg ion FAB): 1025 (M—), 590.

Example 7

Rapamycin 42-ester with 4-(2-hydroxyethyl)piperazine-1-carboxylic acid

A solution of 1-(2-hydroxyethyl)piperazine) (130 mg, 1.0 mmole) in 1 mL dry dichloromethane was added to a solution of 330 mg rapamycin 42-p-nitrophenyl)carbonate (0.31 mmole) in 6 mL dry dichloromethane at −8° under nitrogen and stirred at −8° for 1.5 hours. The reaction mixture was partitioned between dichloromethane and water/brine, the aqueous portion was extracted with dichloromethane, the combined organic portion was washed with brine, dried over MgSO$_4$ and evaporated to a white solid foam. Flash chromatography through silica gel using 2% methanol in dichloromethane yielded 140 mg of the title compound as a white solid, mp 112°–120° C.
IR (KBr): 3450, 2950, 1725, 1650, 1460, 1250 and 995 cm$^{-1}$.
NMR (CDCl$_3$, 400 MHz): δ3.64 (t (J=5.2 Hz), 2 H, H$_d$); 3.51 (broad, 4 H, Ha); 3.39 (s, 3 H, OMe); 3.33 (s, 3 H, OMe); 3.14 (s, 3 H, OMe); 2.57 (t (J=5.2 Hz), 2H, H$_c$); 2.49 (broad, 4 H, H$_b$) ppm. MS (neg. ion FAB): m/z at 1069 (m$^-$), 590.

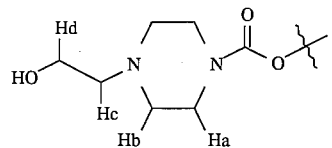

Example 8

Rapamycin 42-ester with 2-(dimethylamino)ethylcarbamic acid salt with hydrochloric acid A solution of 100 mg rapamycin 42-p-nitrophenyl carbonate in 5 ml dichloromethane was treated at 0° under nitrogen with 44 mg N,N-dimethylethylenediamine in 0.5 ml dichloromethane. The reaction mixture was stirred at 0° under nitrogen for ½ hour, diluted with 50 ml dichloromethane, washed with water, and dried with $MgSO_4$. The solvent was evaporated and the residue was dissolved in 1.5 ml dichloromethane. The dichloromethane solution was cooled to 0° under nitrogen and was treated with 1.5 ml 0.1M HCl (gas) in ether. The resulting solution was diluted with 10 ml ether and the hydrochloride salt precipitated out. Stirring was continued at 0° under nitrogen for ¼ hour. The product was collected by filtration, washed with ether, and dried at 54° in vacuum to afford 80 mg of the title product as a white solid, mp 125°–130°.

IR(KBr): 3400 (OH and NH), 1715 ( lactone and ketone C=O), 1640 (amide C=O), 1450, 1240, 1090 and 985 $cm^{-1}$. 1HNMR (DMSO-$D_6$, 400 MHz): δ9.85 (s, 1H, NH+), 7.35 (s, 1H, —OC(O)NH—), 4.40 (m, 1H, $N(CH_3)_2$), 3.26, 3.15, 3.04 (each s, 3H, $OCH_3$), 2.76 (s, 6H, $N(CH_3)_2$) ppm.
MS (neg. ion FAB): 1027.6 ($M^-$), 590.4, 435.3.
C/H/N analysis for $C_{56}H_{89}N_3O_{14} \cdot HCl \cdot 2H_2O$; Calc. 61.09/8.60/3.81; Found 61.06/8.55/3.91.

Example 9

Rapamycin 42-ester with [(4-aminophenyl)methyl]carbamic acid

A solution of 250 mg rapamycin 42-p-nitrophenyl carbonate in 13 ml dichloromethane was treated at −10° under nitrogen with 145 mg 4-aminobenzylamine in 0.5 ml dichloromethane. The reaction mixture was stirred at room temperature under nitrogen for 2 hours, diluted with 150 ml dichloromethane, washed with water and dried with $MgSO_4$. The solvent was evaporated and the residue chromatoghraphed on silica gel. Elution with methanol/dichloromethane (⅔8) afforded 140 mg of the title product as a white solid, mp 107°–110°.

IR (KBr): 3400 (OH and NH), 1720 (lactone and ketone C=O), 1635 (amide C=O), 1520, 1450, 1240, 1100, 985, and 750 $cm^{-1}$. 1HNMR ($CDCl_3$, 400 MHz): δ7.08 (d, J=10 cps, 2H, protons a), 6.65 (d, J=10 cps, 2H, protons b), 4.60 (m, 1H, $C_{42}$—H) 4.24 (d, 2H benzylic protons), 3.39, 3.33, 3.14 (each s, 3H, $OCH_3$) ppm.
MS (neg. ion FAB): 1061.6 ($M^-$), 590.4, 469.3.

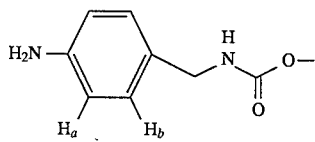

Example 10

Rapamycin 42-ester with [(4-aminophenyl)methyl]carbamic acid salt with hydrochloric acid A solution of 500 mg rapamycin 42-ester with [(4-aminophenyl)methyl] carbamic acid in a mixture of 2 ml ethyl acetate and 8 ml ether was treated at −10° under nitrogen with 0:5 ml 1M HCl (gas) in ether. The hydrochloride salt formed instantly. Stirring was continued at −10° under nitrogen for ¼ hour. The product was collected by filtration, washed with ether, and dried in vacuum to afford 460 mg of the title product as a yellow solid, mp 110°–115° (dec.).

IR (KBr): 3400 (OH and NH), 1715 (lactone and ketone C=O), 1640 (amide C=O), 1505, 1440, 1140, 1090, and 985 $cm^{-1}$. $^1$HNMR (DMSO-$D_6$, 400 MHz): δ7.29 (d, J=10 cps, 2H, protons b), 7.24 (d, J-10 cps, 2H, protons a), 4.40 (m, 1H, $C_{42}$—H), 3.26, 3.15, 3.04 (each s, 3H, $OCH_3$) ppm.

MS (neg. ion FAB): 1061.1 ($m^-$), 590.1, 469.1.

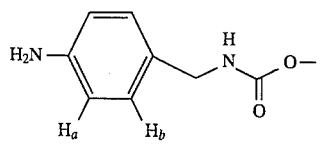

Example 11

Rapamycin 42-ester with (3-dimethylaminopropyl) carbamic acid

A solution of 16.0 g rapamycin 42-p-nitrophenyl carbonate in 250 ml dichloromethane was treated at −10° under nitrogen with 2.96 g 3-dimethylaminopropylamine in 50 ml dichloromethane. The reaction mixture was stirred at 0° under nitrogen for 1.0 hour, diluted with 900 ml dichloromethane, washed with water and dried with $MgSO_4$. The solvent was evaporated and the residue chromatographed on silica gel. Elution with methanol/ethyl acetate (⅓) afforded 7.1 g of the title product as a white solid, mp 104°–106°.

IR (KBr): 3400 (OH and NH), 1715 (lactone and ketone C=O), 1640 (amide C=O), 1440, 1365, 1250, 1100, and 985 $cm^{-1}$. $^1$HNMR ($CDCl_3$, 400 MHz): δ4.55 (m, 1 H, $C_{42}$—H), 3.39, 3.33, 3.14 (each s, 3H, $OCH_3$), 3.25 (t, 2H, —$CH_2$NHC(O)—), 2.35 (t, 2H, —N—$CH_2$ ), 2.22 (s, 6H, $(CH_3)_2N$) ppm.
MS (neg. ion FAB): 1041.6 ($M^-$), 590.4, 449.4.
C/H/N analysis for $C_{57}H_{91}N_3O_{14} \cdot H_2O$; Calc: 64.56/8.84/3.94 Found 64.53/8.80/3.95.

Example 12

Rapamycin 42-ester with (3-dimethylaminopropyl)carbamic acid salt with hydrochloric acid A solution of 520 mg rapamycin 42-ester with (3-dimethylaminopropyl)carbamic acid in a mixture of 4 ml ethyl acetate and 12 ml ether was treated at 0° under nitrogen with 0.75 ml 1M HCl (gas) in ether. The hydrochloride salt formed instantly. Stirring was continued at 0° under nitrogen for ¼ hour. The product was collected by filtration, washed with ether and dried in vacuum to give 460 mg of the title product as a pale solid, mp 108°–112° (dec.).

IR (KBr): 3400 (OH and NH), 1716 (lactone and ketone C=O), 1640 (amide C=O), 1455, 1240, 1100 and 985 $cm^{-1}$. $^1$HNMR (DMSO-$D_6$, 400 MHz): δ4.40 (m, 1H, $C_{42}$—H), 3.27, 3.15, 3.04 (each s, 3H, $OCH_3$), 2.72 (s, 6H, —$N(CH_3)_2$) ppm.
MS (neg. ion FAB); 104 1.6 ($m^-$), 590.4, 449.4.
C/H/N analysis for $C_{57}H_{91}N_3O_{14} \cdot HCl \cdot H_2O$; Calc.: 62.41/8.54/3.83. Found: 62.33/8.66/3.71.

Example 13

Rapamycin 42-ester with (2-diethylamino-ethyl) carbamic acid

A solution of 480 mg rapamycin 42-p-nitrophenyl carbonate in 8 ml dichloromethane was treated at 0° under nitrogen with 136 mg N,N-diethylethylenediamine in 1 ml dichloromethane. The reaction mixture was stirred at 0° under nitrogen for 2 hours, diluted with 200 ml dichloromethane, washed with water and dried with $MgSO_4$. The solvent was evaporated and the residue chromatographed on silica gel. Elution with methanol/dichloromethane (5/95) afforded 405 mg of the title product as a white solid, mp 101°–104°.

IR (KBr): 3400 (OH and NH), 1720 (lactone and ketone C=O), 1650 (amide C=O), 1460, 1350, 110 and 990 cm$^{-1}$. $^1$HNMR (CDCl$_3$, 400 MHz): δ4.54 (m, 1H, C$_{42}$—H), 3.37, 3.31, 3.15 (each s, 3H, OCH$_3$), 2.55 (m, 6H, protons a) 2.70 (m, 2H, protons b) ppm.

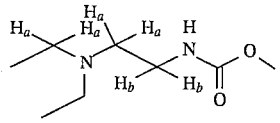

MS (neg. ion FAB): 1055.4 (M$^-$), 590.2, 463.2.

Example 14

Rapamycin 42-ester with (2-diethylamino-ethyl) carbamic acid salt with hdyrochloric acid A solution of 270 mg rapamycin 42-ester with (2-diethylamino-ethyl) carbamic acid in a mixture of 2.5 ml ethyl acetate and 8 ml ether was treated at 0° under nitrogen with 0.26 ml 1M HCl (gas) in ether. The hydrochloride salt formed instantly. Stirring was continued at 0° under nitrogen for ¼ hour. The product was collected by filtration, washed with ether, and dried in vacuum at 50° to afford 170 mg of the title product as a pale solid, mp 101°–106°.
IR (KBr): 3400 (OH and NH), 1720 (lactone and ketone C=O), 1650 (amide C=O), 1450, 1400, 1250, 1100 and 990 cm$^{-1}$. $^1$HNMR (DMSO-D$_6$, 400 MHz): δ4.39 (m, 1H, C$_{42}$—H), 3.25, 3.15, 3.04 (each s, 3H, OCH$_3$), 3.05–3.13 (m, 8 H, —CH$_2$—N—), 1.19 (t, 6H, —N—C—CH$_3$) ppm.
MS (neg. ion FAB): 1055.7 (M$^-$), 590.3, 463.3.

Example 15

Rapamycin 42 -ester with (2-diethylamino-ethyl) carbamic acid salt with maleaic acid A solution of 540 mg rapamycin 42-ester with (2-diethylamino-ethyl) carbamic acid in a mixture of 5 ml ethyl acetate and 5 ml ether was treated at room temperature under nitrogen with 60 mg maleic acid in a mixture of 1 ml ethyl acetate and 1 ml ether. The resulting mixture became cloudy and turned into a suspension, which was warmed to 50° to get a solution. The clear solution was evaporated at 50° under reduced pressure and dried in vacuum to afford 560 mg of the title product as a white solid, mp 101°–105°.
IR (KBr): 3410 (OH and NH), 1720 (lactone, ketone and acid C=O), 1650 (amide C=O), 1460, 1400, 1350, 1250, 1100, and 995 cm$^{-1}$. $^1$HNMR (DMSO-D$_6$): δ6.03 (s, 2H, maleate olefin), 4.40 (m, 1 H, C$_{42}$—H), 3.27, 3.16, 3.05 (each s, 3H, OCH$_3$), 3.26–3.16 (m, 8H, —CH$_2$—N), 1.18 (t, 6H, CH$_3$—C—N<) ppm.
MS (neg. ion FAB): 1055.7 (M$^-$), 590.4, 463.0.

Example 16

Rapamycin 42 -ester with (2-diethylamino-ethyl)carbamic acid salt with citric acid A solution of 528 mg rapamycin 42-ester with (2-diethylamino-ethyl) carbamic acid in a mixture of 2 ml ethyl acetate and 8 ml ether was treated at room temperature with 96 mg citric acid in 1 ml methanol. The resulting solution was stirred at room temperature under nitrogen for ¼ hour. The solvent was evaporated and the residue was dried in vacuum at 50° to afford 590 mg of the title product as a white solid, mp 6°–100°.
IR (KBr): 3430 (OH and NH), 1720 (lactone, ketone and acid C=O), 1640 (amide C=O), 1440, 1250, 1190, 1090 and 995 cm$^{-1}$. $^1$HNMR (DMSO-D$_6$): δ7.24 (m, 1 H, —NHCO), 4.38 (m, 1 H, C$_{42}$—H), 3.25, 3.14, 3.08 (each s, 3 H, OCH$_3$), 1.11 (t, 6H, —N—C—CH$_3$) ppm.
MS (neg. ion FAB): 1055.6 (m$^-$), 590.3, 463.0.

Example 17

Rapamycin 42-ester with 4(1-ethyl-pyrrolidin-2-ylmethyl)carbamic acid

A solution of 480 mg rapamycin 42-p-nitrophenyl carbonate in 5 ml dichloromethane was treated at −10° under nitrogen with 128.2 mg 2-(aminomethyl)-1-ethylpyrrolidine in 1 ml dichloromethane. The reaction mixture was stirred at 0°/N$_2$ for 4 hours and at room temperature/N$_2$ for ½ hour, diluted with 150 ml dichloromethane, washed with water, and dried with MgSO$_4$. The solvent was evaporated and the residue chromatographed on silica gel. Elution with methanol/dichloromethane (5/95) afforded 171 mg of the title product as pale yellow solid, mp 115°–118°.
IR (KBr): 3400 (OH and NH), 1715 (lactone and ketone C=O), 1640 (amide C=O), 1450, 1250, 1100, and 990 cm$^{-1}$. $^1$HNMR (CDCl$_3$, 400 MHz): δ4.55 (m, 1 H, C$_{42}$—H), 3.36, 3.32, 3.12 (each s, 3 H, OCH$_3$) ppm.
MS (neg. ion FAB): 1067.2 (M$^-$), 590.1, 475.1.

Example 18

Rapamycin 42-ester with 4-(1-ethyl-pyrrolidin-2-ylmethyl)-carbamic acid salt with hydrochloric acid A solution of 520 mg rapamycin 42-ether, with 4-(1-ethyl-pyrrolidin-2-ylmethyl) carbamic acid in a mixture of 6 ml ethyl acetate and 10 ml dry ether was treated at 0° under nitrogen with 0.5/ml 1M HCl (gas) in ether. The hydrochloride salt formed instantly. Stirring was continued at 0° under nitrogen for ½ hour. The product was collected by filtration, washed with ether and dried in vacuum at 54° for 16 hours to give 360 mg of the title product as a pale solid, mp 113°–120° (dec).
IR (KBr): 3400 (OH and NH), 1720 (lactone and ketone C=O), 1650 (amide C=O), 1455, 1250, 1100, and 990 cm$^{-1}$. $^1$HNMR (DMSO-D$_6$, 400 MHz): δ4.40 (m, 1 H, C$_{42}$—H), 3.27, 3.15, 3.05 (each s, 3 H, OCH$_3$) ppm.
MS (neg. ion FAB): 1067.2 (M$^-$), 590.1, 475.1. C/H/N/ analysis for C$_{59}$H$_{93}$N$_3$O$_{14}$·HCl·H$_2$O; Calc.: 63.10/8.61/3.7; Found; 63.01/8.58/3.63.

Example 19

Rapamycin 42-ester with piperidine-1-carbamic acid

A solution of 25 g rapamycin 42-p-nitrophenyl carbonate in 11 ml N,N-dimethylformamide was treated at room temperature under nitrogen with 714 mg 1-aminopiperidine. The reaction mixture was stirred at room temperature for five hours. The solvent was removed by vacuum pump and the residue was dissolved in 300 ml dichloromethane. The organic solution was washed with water, dried with MgSO$_4$, evaporated, and the residue chromatographed on silica gel. Elution with methanol/dichloromethane (1.5/98.5) afforded 470 mg of the title product as a white solid, mp 110°–115°.
IR (KBr): 3420 (OH and NH), 1715 (lactone and ketone C=O), 1640 (amide C=O), 1450, 1235, 1100, and 990 cm$^{-1}$. $^1$HNMR (CDCl$_3$, 400 MHz): δ4.55 (m, 1 H, C$_{42}$—H), 3.38, 3.33, 3.14 (each s, 3 H, OCH$_3$), 2.73 (m, 4 H, protons a), 1.65 (m, 6 H, protons b) ppm.

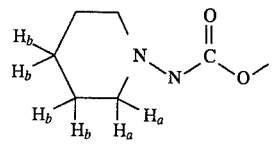

MS (neg. ion FAB): 1039.6 (M⁻), 590.4, 447.3.

Example 20

Rapamycin 42-ester with pipefidine-1-carbamic acid hydrochloric acid salt

A solution of 25/mg rapamycin 42-ester with piperidine-1-carbamic acid in a mixture of 1 ml ethyl acetate and 4 ml dry ether was treated at 0° under nitrogen with 0.36 ml of 1M HCl (gas) in ehter. The hydrochloride salt formed instantly. Stirring was continued at 0° under nitrogen for ¼ hour. The product was collected by filtration, washed with ether, and dried in vacuum to afford 130 mg of the title product as a white solid, mp 120°–125°.
IR (KBr): 3400 (OH and NH), 1735 (lactone and ketone C=O), 1640 (areire C=O), 1450, 1370, 1240, 1100, and 990 cm⁻¹. ¹HNMR (DMSO-D₆, 400 MHz): δ4.75 (m, 1 H, $C_{42}$—H), 3.26, 3.15, 3.04 (each s, 3 H, OCH₃) ppm.
MS (neg. ion FAB): 1039.5 (M⁻), 590.4, 447.3.

Example 21

Rapamycin 42-ester with [(3 R)-(+)-3-aminopyrrolidine] carboxylic acid

A solution of 2.67 g rapamycin 42-p-nitrophenyl carbonate in 23 ml dichloromethane was treated at 0° under nitrogen with 213 mg of (3 R)-(+)-3-aminopyrrolidine in 1 ml dichloromethane. The reaction mixture was stirred at room temperature under nitrogen for two hours, diluted with 300 ml ethyl acetate, washed with water, and dried with MgSO₄. The solvent was evaporated and the residue chromatographed on silica gel. Elution with dichloromethane/methanol (94/6) afforded 1.1 g of the title product as a pale yellow solid, mp 100°–105°.
IR (KBr): 3420 (OH and NH), 1715 (lactone and ketone C=O), 1640 (amide C=O), 1450, 1420, 1190, 1100, and 990 cm⁻¹. ¹HNMR (CDCl₃, 400 MHz): δ4.54 (m, 1 H, $C_{42}$—H), 3.50–3.60, (m, 5 H, protons a), 3.39, 3.33, 3.14 (each s, 3H, OCH₃) ppm.
MS (neg. ion FAB): 1025.5 (M⁻), 590.3, 433.3.

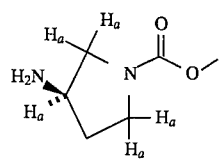

Example 22

Rapamycin 42-ester with [(3 R)-(+)-3-aminopyrrolidine] carboxylic acid hydrochloric acid salt A solution of 190 mg of rapamycin 42-ester with [(3 R)-(+)-3-amino-pyrrolidine]carboxylic acid in a mixture of 6 ml ethyl acetate and 6 ml dry ether was treated at 0° under nitrogen with 0.3 ml of 1M HCl (gas) in ether. The clear solution was evaporated to a volume of about 4 ml and diluted with 15 ml ether. The crystalline hydrochloride salt formed, and was stirred at 0° under nitrogen for ¼ hour. The product was collected by filtration, washed with ether, and dried in vacuum to afford 150 mg of the title product as a pale solid, mp 147°–152° (dec).
IR (KBr): 3420 (OH and NH), 1715 (lactone and ketone C=O), 1640 (amide C=O), 1440, 1190, 1100, and 990 cm⁻¹.
¹HNMR (DMSO-D₆, 400 MHz): δ4.35 (m, 1 H, $C_{42}$—H), 3.32, 3.15, 3.04 (each s, 3 H, OCH₃), 3.40–3.80 (m, 5 H, protons a) ppm.

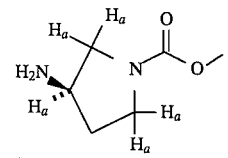

C/H/N/analysis for C₅₇H₈₉N₃O₁₄·H₂O·HCl Calc.: 62.23/ 8.28/3.88; Found 61.93/8.26/3.91.

Example 23

Rapamycin 42-ester with [(3S)-(–)-3-aminopyrrolidine] carboxylic acid

A solution of 3.0 rapamycin 42-p-nitrophenyl carbonate in 20 ml dichloromethane was treated at 0° under nitrogen with 319 mg of (3S)-(–)-3-aminopyrrolidine in 2 ml dichloromethane. The yellow solution was stirred at room temperature for 3 hours, diluted with 100 ml dichloromethane, washed with water, and dried with MgSO₄. The solvent was evaporated and the residue chromatographed on silica gel. Elution with dichloromethane/methanol (93/7) afforded 1.32 g of the title product as a pale white solid, mp 135°–140°.
IR (KBr): 3400 (OH and NH), 1715 (lactone and ketone C=O), 1640 (amide C=O), 455, 1420, 1190, 1100 and 990 cm⁻¹. ¹HNMR (CDCl₃, 400 MHz): δ4.55 (m, 1 H, $C_{42}$—H), 3.59, (m, 3 H, protons a), 3.20 (t. 2 H, protons b), 3.39, 3.33, 3.14 (each s, 3 H, OCH₃) ppm.
MS (neg. ion FAB): 1025.3

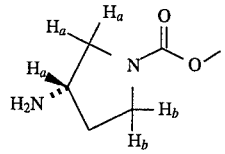

(M⁻), 590.2, 433.2.

Example 24

Rapamycin 42-ester with [(3 S)-(–)-3-aminopyrrolidine] carboxylic acid salt with hydrochloric acid A solution of 700 mg of rapamycin 42-ester with [(3 S)-(–)-3-aminopyrrolidine]carboxylic acid in a mixture of 4 ml ethyl acetate and 4 ml ether was treated at 0° under nitrogen with 0.75 ml of 1M HCl (gas) in ether. The clear solution was diluted with 4 ml ether to induce crystalline salt formation. Stirring was continued at 0° under nitrogen for ¼ hour. The product was collected by filtration, washed with ether, and dried in vacuum to afford 610 mg of the title product as a white solid, mp 136°–140° (dec).
IR (KBr): 3500 (OH and NH), 1715 (lactone and ketone C=O), 1640 (amide C=O), 1440, 1190, 1100, and 990 cm⁻¹.
¹HNMR (DMSO-D₆, 400 MHz): δ8.13 (s, 2 H, NH₂), 4.36 (m, 1 H, $C_{42}$—H), 3.63–3.40 (m, 5 H, protons a), 3.32, 3.15, 3.04 (each s, 3 H, OCH₃) ppm.

MS (neg. ion FAB): 1025.6 (M—), 590.4, 433.3.

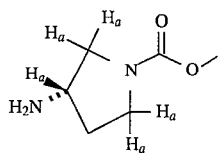

C/H/N analysis for $C_{57}H_{89}N_3O_{14} \cdot H_2O \cdot HCl$; Calc: 62.23/8.28/3.88; Found 62,15/8,33/3,88

Example 25

Rapamycin 42-ester with [1-(4-morpholinyl)propyl]carbamic acid

A solution of 9.0 g rapamycin 42 p-nitrophenyl carbonate in 50 ml dichloromethane was treated at 0° under nitrogen atmosphere with 2.3 g 4-(3-aminopropyl) morpholine in 4 ml dichloromethane. The reaction mixture was stirred at 0°/$N_2$ for two hours, diluted with 400 ml dichloromethane, washed with water, and dried with $MgSO_4$. The solvent was evaporated and the residue chromatographed on silica gel. Eultion with ethyl acetate/methanol (9/1) afforded 6.70 g of the title product as a white solid, mp 96°–99°.
IR (KBr): 3400 (OH and NH), 1745 (lactone and ketone C=O), 1650 (areire C=O), 1450, 1250, 1120 and 990 $cm^{-1}$.
$^1$HNMR ($CDCl_3$, 400 MHz): a 4.54 (m, 1 H, $C_{42}$—H), 3.70, (t. 4 H, protons c), 3.37, 3.33, 3.14 (each s, 3H, $OCH_3$), 3.23 (t, 2 H, protons b), 2.43 (t, 6H, protons a) ppm.

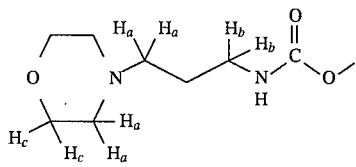

MS (neg. ion FAB): 1083.7 (M—), 590.4, 491.3.

Example 26

Rapamycin 42-ester with [1-(4-morpholinyl)propyl]carbamic acid salt with hydrochloric acid A solution of 530 mg rapamycin 42-ester with [1-(4-morpholinyl)propyl]carbamic acid in a mixture of 3.5 ml ethyl acetate and 7.0 ml ether was treated at 0° under nitrogen with 0.5/ml 1M HCl (gas) in ether. The hydrochloride salt formed instantly. Stirring was continued at 0° under nitrogen for ¼ hour. The product was collected by filtration, washed with ether, and dried in vacuum at room temperature to afford 490 mg of the title product as a white solid, mp 106°–110° (dec).
IR (KBr): 3400 (OH and NH), 1715 (lactone and ketone C=O), 1645 (amide C=O), 1450, 1240, 1100, and 980 $cm^{-1}$.
$^1$HNMR (DMSO-$D_6$, 400 MHz): δ4.37 (m, 1 H, $C_{42}$—H), 3.24, 3.12, 3.02 (each s, 3 H, $OCH_3$), 7.23 (s, 1 H, NH) ppm.
MS (neg. ion FAB): 1083.3 (M—), 590.2, 491.2.
C/H/N analysis for $C_{59}H_{93}N_3O_{15} \cdot HCl \cdot H_2O$; Calc: 62.22/8.32/3.68; Found 61.98/8.49/3.43.

Example 27

Rapamycin 42-ester with (4-morpholinyl)propyl carbamic acid salt with maleic acid A solution of 552 mg rapamycin 42-ester with (4-morpholinyl) propyl carbamic acid in a mixture of 5 ml ethyl acetate and 5 ml ether was treated at room temperature under nitrogen with 60 mg maleic acid in a mixture of 1 ml ethyl acetate and 1 ml ether. The solvent was evaporated leaving 550 mg title product as a white solid, mp 104°–107°.
IR (KBr): 3430 (OH and NH), 1725 (lactone and ketone C=O), 1650 (amide C=O), 1450, 1355, 1350, 1250, 1100, and 990 $cm^{-1}$. $^1$HNMR (DMSO-$D_6$): δ7.1 (s, 1 H, —NH), 6.05 (s, 2 H, maleate olefin), 4.39 (m, 1 H, $C_{42}$—H), 3.27, 3.16, 3.05 (each s, H, $OCH_3$) ppm.
MS (neg. ion FAB): 1083.8 (M—), 590.5,491.5.
C/H/N analysis for $C_{63}H_{97}N_3O_{19} \cdot 2H_2O$; Calc: 61.19/8.23/3.39; Found 0.95/8.05/3.32.

Example 28

Rapamycin 42-ester with (4-morpholinyl)propyl carbamic acid salt with citric acid A solution of 528 mg rapamycin 42-ester with (4-morpholinyl) propyl carbamic acid in a mixture of 2 ml ethyl acetate and 8 ml ether was treated at room temperature under nitrogen with 96 mg citric acid in 1 ml methanol. The resulting solution was stirred at room temperature for ¼ hour. The solvent was evaporated to dryness to afford 620 mg of the title product as a white solid, mp 102°–106° (dec).
IR (KBr): 3420 (OH and NH), 1720 (lactone and ketone, acid C=O), 1650 (amide C=O), 1450, 1250, 1100, and 990 $cm^{-1}$. $^1$HNMR (DMSO-$D_6$, 400 MHz): δ8.30 (s, 1 H, NH+), 7.12 (t, 1 H, NHCO—), 4.38 (m, 1 H, $C_{42}$—H), 3.60 (t, 4 H, —$CH_2$—O—$CH_2$), 3.26, 3.14, 3.04 (each s, 3 H, $OCH_3$)ppm.
MS (Neg. ion FAB): 1083.6 (M—), 590.4, 491.4.

Example 29

Rapamycin 42-ester with (4-morpholinyl)propyl carbamic acid salt with methanesulfonic acid To a solution of 0.400 g (0.37 mmol) of the compound of Example 25 in ether was added dropwise 8.1 ml (0.35 retool) of 0.043M solution of methanesulphonic acid in ether. The resulting precipitate was collected. The solid was triturated with ether, filtered under a cone of nitrogen, and dried under vacuum to give 0.365 g (84%) of the title compound as a white solid.
Calcd for $C_{59}H_{93}N_3O_{15} \cdot CH_3SO_3H \cdot 3H_2O$ : C, 58.37; H, 8.41; N, 3.40. Found: C, 58.68; H, 8.24; N, 3.47.

Example 30

Rapamycin 42-ester with (4-morpholinyl)propyl carbamic acid salt with phosphoric acid To a solution of 0.500 g (0.461 retool) of the compound of Example 25 in ether was added dropwise 4.52 ml (0.438 retool) of 0.102M solution of phosphoric acid in methanol. The reaction mixture was stined under nitrogen for about 30 minutes after which time the solvents were removed under vacuum. The residue was triturated with ether, filtered under a cone of nitrogen, and dried under vacuum to give 0.480 g (93% ) of the title compound as a cream colored solid.
Calcd for $C_{59}H_{93}N_3O_{15} \cdot H_3PO_4 \cdot 4H_2O$ : C, 56.51; H, 8.36; N, 3.35. Found: C, 56.62; H, 8.07; N, 3.40.

Example 31

Rapamycin 42-ester with (4-morpholinyl)propyl carbamic acid salt with L-monomethyl taratic acid To a solution of 0.550 g (0.507 mmol) of the compound of Example 25 in ether was added dropwise 7.57 ml (0.507 mmol) of 0.067M solution of L (+) tartaric acid monomethyl ester in methanol. The reaction mixture was stirred under nitrogen for about 30 minutes after which time the solvents were removed under vacuum. The residue was triturated with ether, filtered under a cone of nitrogen, and dried under vacuum to give 0.476 g (75%) of the title compound as a cream colored solid.
Calcd for $C_{59}H_{93}N_3O_{15} \cdot C_5H_8O_6 \cdot 1.5H_2O$ : C, 60.26; H, 8.22; N, 3.29. Found: C, 60.05; H, 8.08; N, 3.27.

Example 32

Rapamycin 42-ester with (4-morpholinyl)propyl carbamic acid salt with L-tartaric acid To a solution of 0.330 g (0.304 retool) of the compound of Example 25 in ether was added dropwise 2.89 ml (0.289 retool) of 0.1M solution of L(+) tartaric acid in methanol. The reaction mixture was stirred under nitrogen for about 30 minutes after which time the solvents were removed under vacuum. The residue was triturated with ether, filtered under a cone of nitrogen, and dried under vacuum to give 0.307 g (86%) of the title compound as a cream colored solid.
Calcd for $C_{59}H_{93}N_3O_{15} \cdot C_4H_6O_6 \cdot 2 H_2O$ : C, 59.58; H, 8.18; N, 3.31. Found :C, 59.46; H, 8.30; N, 3.44.

Example 33

Rapamycin 42-ester with (4-morpholinyl)propyl carbamic acid salt with fumaric acid To a solution of 0.330 g (0.304 retool) of the compound of Example 25 in ether was added dropwise 2.89 ml (0.289 retool) of 0.1M solution of fumaric acid in methanol. The reaction mixture was stirred under nitrogen for about 30 minutes after which time the solvents were removed under vacuum. The residue was triturated with ether, filtered under a cone of nitrogen, and dried under vacuum to give 0.197 g (57%) of the title compound as a cream colored solid.
Calcd for $C_{59}H_{93}N_3O_{15} \cdot C_4H_4O_4 \cdot 2.5H_2O$ : C, 60.78; H, 8.26; N, 3.37. Found: C, 60.68; H, 8.05; N, 3.42.

Example 34

Rapamycin 42-ester with (4-morpholinyl)propyl carbamic acid salt with sulfuric acid To a solution of 0.330 g (0.304 retool) of the compound of Example 25 in ether was added dropwise 1.60 ml (0.289 retool) of 0.18M solution of sulfuric acid in ether. The reaction mixture was stirred under nitrogen for about 30 minutes after which time the solvents were removed under vacuum. The residue was triturated with ether, filtered under a cone of nitrogen, and dried under vacuum to give 0.308 g (90%) of the title compound as a cream colored solid.
Calcd for $C_{59}H_{93}N_3O_{15} \cdot H_2SO_4 \cdot 3H_2O$ : C, 57.33; H, 8.23; N, 3.40. Found: C, 57.45; H, 8.13; N, 3.45.

Example 35

Rapamycin 42-ester with (4-morpholinyl)propyl carbamic acid salt with D-tartaric acid acid To a solution of 0.330 g (0.304 retool) of the compound of Example 25 in ether was added dropwise 2.89 ml (0.289 retool) of 0.1M solution of D(−) tartaric acid in methanol. The reaction mixture was stirred under nitrogen for about 30 minutes after which time the solvents were removed under vacuum. The residue was triturated with ether, filtered under a cone of nitrogen, and dried under vacuum to give 0.279 g (78%) of the title compound as a cream colored solid.
Calcd for $C_{59}H_{93}N_3O_{15} \cdot C_4H_6O_6 \cdot 2.5H_2O$ : C, 59.16; H, 8.19; N, 3.28. Found: C, 59.16; H, 8.27; N, 3.10.

Example 36

Rapamycin 42-ester with [2-(1-morpholinyl)ethyl]carbamic acid

A solution of 1.6 g rapamycin 42-p-nitrophenyl carbonate in 10 ml dichloromethane was treated at −10° under nitrogen atmosphere with 390 mg 4-(2-aminoethyl)-morpholine in 2 ml dichloromethane. The reaction mixture was stirred at room temperature under $N_2$ for 1 ¾ hours, diluted with 200 ml dichloromethane, washed with water, and dried with $MgSO_4$. The solvent was evaporated and the residue chromatographed on silica gel. Elution with 2.5–3.0% methanol in dichloromethane afforded 0.88 g the title product as a white solid, top. 110°–113°.
IR (KBr): 3400 (OH and NH), 1720 (lactone and ketone C=O), 1645 (amide C=O), 1450, 1110, and 985 cm$^{-1}$.
$^1$HNMR (CDCl$_3$, 400 MHz): a 4.55 (m, 1 H, C$_{42}$—H), 3.70, (m, 4 H, —O—CH$_2$—C—N—), 3.39, 3.33, 3.14 (each s, 3 H, OCH$_3$), 2.46 (m, 6 H,

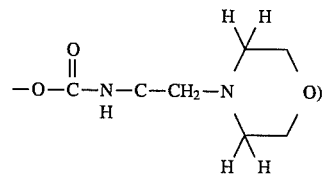

ppm.
MS (neg. ion FAB): 1069.9 (M−), 590.5, 477.5.

Example 37

Rapamycin 42-ester with [2-(1-morpholinyl)ethyl]carbamic acid salt with hydrochlroic acid.

A solution of 550 mg rapamycin 42-ester with [2-(1-morpholinyl)ethyl]carbamic acid in 15 ml dry ether was treated at 0° under $N_2$ with 0.76 ml 1M HCl (gas) in ether. The hydrochloride salt formed instantly. Stirring was continued at 0°/$N_2$ for ¼ hour. The product was collected by filtration, washed with ether, and dried in vacuum to afford 450 mg of the title product as a white solid, mp 110°–113°.
IR (KBr): 3400 (OH and NH), 1725 (lactone and ketone C=O), 1640 (amide C=O), 1450, 1250, 1100, and 988 cm$^{-1}$.
$^1$HNMR (DMSO-D$_6$, 400 MHz): δ4.38 (m, 1 H, C$_{42}$—H), 3.97 (t, 4 H, —CH$_2$—O—CH$_2$—), 3.24, 3.13, 3.06 (each s, 3H, OCH$_3$) ppm.
MS (Neg. ion FAB): 1069.5 (M−), 590.3, 477.3.

Example 38

Rapamycin 42-ester with [(4-methylpiperazin-1-yl)propyl]carbamic acid

A solution of 1.0 g rapamycin 42-p-nitrophenyl carbonate in 15 ml dichloromethane was treated at 0° under $N_2$ with 157 mg 1-(3-aminopropyl) 4-methylpiperazine in 1 ml dichloromethane. The reaction mixture was stirred at room temperature under $N_2$ for 3 ¼ hours, diluted with 200 ml dichloromethane, washed with water, and dried with $MgSO_4$. The solvent was evaporated and the residue chromatographed on silica gel. Elution with 7% methanol in dichloromethane afforded 470 mg the title product as a white foam, mp 100°–105°.
IR (KBr): 3430 (OH and NH), 1735 (lactone and ketone C=O), 1650 (amide C=O), 1530, 1465, 1385, 1260, 1115, and 1000 cm$^{-1}$. $^1$ HNMR (DMSO-D$_6$, 400 MHz): δ 4.53 (m, 1 H, C$_{42}$—H), 3.38, 3.33. 3.14 (each s, 3 H, OCH$_3$), 2.32 (s, 3 H, —N—CH₃ ) ppm.
MS (Neg. ion FAB): 1096.6 (M⁻), 590.3,504.4.

Example 39

Rapamycin 42-ester with [(4-methylpiperazin-1-yl)propyl]carbamic acid salt with hydrochloric acid A solution of 244 mg rapamycin 42-ester with [(4-methylpiperazin-1-yl)propyl]carbamic acid in a mixture of 4 ml ethyl acetate and 6 ml dry ether was treated at 0° under $N_2$ with 0.33 ml 1M HCl (gas) in ether. The hydrochloride salt formed instantly. Stirring was continued at 0°/$N_2$ for ¼ hour. The product was collected by filtration, washed with ether, and dried in vacuum to afford 158 mg of the title product as a white solid, mp 125°–130°.
IR (KBr): 3420 (OH and NH), 1725 (lactone and ketone C=O), 1650 (amide C=O), 1520, 1450, 1400, 1250, 1110, and 990 cm⁻¹. ¹HNMR (DMSO-$D_6$, 400 MHz): a 4.37 (m, 1 H, $C_{42}$—H), 3.26, 3.14. 3.04 (each s, 3 H, OCH₃), 2.68 (s, 3 H, —N—CH₃ ) ppm.
MS (Neg. ion FAB): 1096.6 (M⁻), 590.3,504.4.

Example 40

Rapamycin 42-ester with (N,N-di-n-butylaminopropyl)-carbamic acid

A solution of 1.0 g of rapamycin 42-p-nitrophenylcarbonate in 15 ml dichloromethane was treated at −10° under a nitrogen atmosphere with 360 mg N,N-di-n-butyl-1.3-propylanediamine in 2 ml dichloromethane. The yellow solution was stirred at 0° under a nitrogen atmosphere for 3 ½ hours. The reaction mixture was diluted with 200 ml dichloromethane, washed with water, dried with $MgSO_4$ and evaporated. The residue was chromatographed on silica gel. Elution with 5% methanol in dichloromethane afforded 490 mg of the title compound as a white foam, mp. 100°–105°.
IR (KBr): 3450 (OH and NH), 1745 (lactone and ketone C=O), 1640 (amide C=O), 1450, 1340, 1250, 1100 and 990 cm⁻¹. ¹HNMR (CDCl₃, 400 MHz): δ4.54 (m, 1 H, $C_{42}$—H), 3.38, 3.33.3.13 (s, 3 H, OCH₃), 0.933 (t, terminal CH₃ of butyl) ppm.
MS (Neg. ion FAB): 1125.6 (M⁻), 590.3,299.3, 167.1.

Example 41

Rapamycin 42-ester with (N,N-di-n-butylaminopropyl)-carbamic acid salt with hydrochloric acid A solution of 300 mg rapamycin 42-ester with N,N-di-n-butylaminopropyl)carbamic acid in a mixture of 1 ml ethyl acetate and 4 ml ether was treated at −78° under $N_2$ with 0.8 ml 1M HCl (gas) in ether. The hydrochloride salt formed instantly. Stirring was continued at −78° under $N_2$ for ½ hour. The product was collected by filtration, washed with ether, and dried in vacuum to afford 245 mg of the title product as a whte solid, mp 115°–120°.
IR (KBr): 3400 (OH and NH), 1725 (lactone and ketone C=O), 1540, 1450, 1400, 1250, 1000, and 990 cm⁻¹. ¹HNMR (DMSO-$D_6$, 400 MHz): a 4.37 (m, 1 H, $C_{42}$—H), 3.04, 3.14. 3.35 (each s, 3H, OCH₃), 0.90 (t, terminal CH₃ of butyl)ppm.
MS (Neg. ion FAB): 1125.6 (M⁻), 590.3,533.4, 229.3, 167.1.

The following representative compounds were prepared from rapamycin 42-p-nitrophenyl carbonate and the appropriate amine by employing the method used to prepare the compound of Example 9.

Example 42

Rapamycin 42-ester with [2-(4-pyrimidin-2-yl-piperazin-1-yl)-ethyl]carbamic acid, m.p. 103°–106° C.

Example 43

Rapamycin 42-ester with [2-(morpholine-4-carbonyloxy)-ethyl]carbamic acid, m.p. 97–100° C.

Example 44

Rapamycin 42-ester with {2-[2-(pyridin-2-yl-ethyl)carbamoyloxy]-ethyl}carbamic acid, m.p. 89°–92° C.

Example 45

Rapamycin 42-ester with 4-(pyridin-2-yl)-piperazine-1-carboxylic acid, m.p. 118°–100° C.

Example 46

Rapamycin 42-ester with [3-(imidazol-1-yl)propyl]-carbamic acid, m.p. 103°–106° C.

Example 47

Rapamycin 42-ester with 4-benzyl-piperazine-1-carboxylic acid, m.p. 111°–120° C.

Example 48

Rapamycin 42-ester with 4-(pyrimidin-2-yl)-piperazine-1-carboxylic acid, m.p. 117°–126° C.

Example 49

Rapamycin 42-ester with 4-phenyl-piperazine-1-carboxylic acid, m.p. 119°–126° C.

Example 50

Rapamycin 42-ester with benzimidazole-1-carboxylic acid, m.p. 122°–133° C.

Example 51

Rapamycin 42-ester with [2-(1-methyl-pyrrolidin-2-yl)-ethyl]carbamic acid, m.p. 99°–102° C.

Example 52

Rapamycin 42-ester with (pyridin-2-ylmethylene)-hydrazine-carboxylic acid, m.p. 128°–132° C.

Example 53

Rapamycin 42-ester with [4-(2-hydroxyethyl)-piperazin-1-yl]-carbamic acid, m.p. 115°–1120° C.

What is claimed is:
1. A pharmaceutical composition comprising a compound of the structure

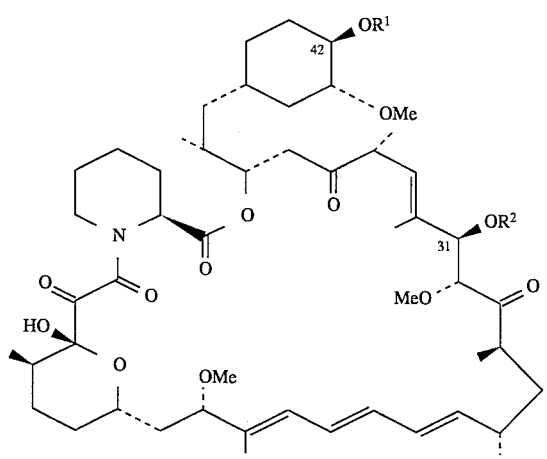

wherein R¹ and R² are each, independently, hydrogen, —CONH—q—B;

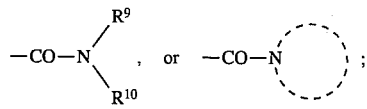

R³, R⁴, R⁵, and. R⁶ are each, independently, hydrogen, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, arylalkyl of –7–10 carbon atoms, cycloalkyl of 3–8 carbon atoms, —OR⁷, —SR⁷, halogen, —CN, —NO₂, —CF₃, —COR⁷, —CO₂R⁷, —CONHR⁷, —SO₂R⁷, —OSO₃R⁷, —NR⁷R⁸, —NHCOR⁷, —NHSO₂R⁷, or Ar;

B is hydrogen, alkenyl of 2–7 carbon atoms, alkynyl of 2–7 carbon atoms, hydroxyalkyl of 1–6 carbon atoms alkylthioalkyl of 2–12 carbon atoms, alkylaminoalkyl of 2–12 carbon atoms. dialkylaminoalkyl of 3–12 carbon atoms. —OR⁷, —SR⁷, —CN, —CF₃, —COR⁷, —CONHR⁷, —OSO₃R⁷, —NR⁷R⁸, —NHCOR⁷, —NHSO₂R⁷, or Ar:

R⁷ and R⁸ are each, independently, hydrogen, alkyl of 1–6 carbon atoms, arylalkyl of 7–10 carbon atoms, alkenyl of 2–7 carbon atoms, alkynyl of 2–7 carbon atoms, hydroxyalkyl of 1–6 carbon atoms, alkoxyalkyl of 2–12 carbon atoms, alkylthioalkyl of 2–12 carbon atoms, alkylaminoalkyl of 2–12 carbon atoms, dialkylaminoalkyl of 3–12 carbon atoms, cycloalkyl of 3–8 carbon atoms, or Ar;

R⁹ and R¹⁰ are each, independently, alkyl of 1–6 carbon atoms, alkenyl of 2–7 carbon atoms, alkynyl of 2–7 carbon atoms, hydroxyalkyl of 1–6 carbon atoms, alkoxyalkyl of 2–12 carbon atoms, —CF₃, —COR⁷, —CO₂R⁷, —CONHR⁷, —SO₂R⁷, or Ar; carbon atoms, alkylthioalkyl of 2–12 carbon atoms, alkylaminoalkyl of 2–12 carbon atoms, dialkylaminoalkyl of 3–12 carbon atoms, arylalkyl of 7–10 carbon atoms, cycloalkyl of 3–8

A is —CH₂—, —NR⁷—, —O—, —S—, —SO—, —PR⁷—, —NHCO—, —NHSO—, or —P(O)(R⁷)—;

Ar is naphthyl, pyridyl, quinolyl, isoquinolyl, quinoxalyl, thienyl, thionaphthyl, furyl, benzofuryl, benzodioxyl, benzoxazolyl, benzoisoxazolyl, indolyl, thiazolyl, isoxazolyl, pyrimidinyl, pyrazinyl, imidazolyl, benzopyranyl, benzthiophenolyl, benzimidazolyl, benzthiazolyl, benzodioxolyl, piperidinyl, morpholinyl, piperazinyl, tetrahydrofuranyl, or pyrrolidinyl; wherein the Ar group may be optionally mono-, di-, or tri- substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromethyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO₃H, —PO₃H, and —CO₂H;

is a nitrogen containing heterocyclic radical selected from the group consisting of pyridyl, pyrazinyl, pipcridinyl, morpholinyl, pipcrazinyl, pyrrolidinyl, thiazolyl, pyrimidinyl, isoxazolyl, pyrrolidinyl, and imidazolyl may be optionally mono-, di-, or tri-substituted with a group selected from alkyl of 1–6 carbon atoms, arylalkyl of 7–10 carbon atoms, alkoxy of 1–6 carbon atoms, cyano, halo, hydroxy, nitro, carbalkoxy of 2–7 carbon atoms, trifluoromcthyl, amino, dialkylamino of 1–6 carbon atoms per alkyl group, dialkylaminoalkyl of 3–12 carbon atoms, hydroxyalkyl of 1–6 carbon atoms, alkoxyalkyl of 2–12 carbon atoms, alkylthio of 1–6 carbon atoms, —SO₃H, —PO₃H, and ≤CO₂H;
with the proviso that R¹ and R² are not both hydrogen and further provided that B is not hydrogen if q is 1;
m=0–6;
n=0–6;
p=0–1;
q=0–1;
or a pharmaceutically acceptable salt thereof and a pharmaceutical carrier.

\* \* \* \* \*